United States Patent
Just et al.

(10) Patent No.: US 11,612,120 B2
(45) Date of Patent: Mar. 28, 2023

(54) POWDERY MILDEW RESISTANT PEPPER PLANTS

(71) Applicant: Seminis Vegetable Seeds, Inc., St. Louis, MO (US)

(72) Inventors: Brian J. Just, Fort Myers, FL (US); Joel M. Kniskern, Sacramento, CA (US); Rebeca Noelani Schauland, Davis, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 169 days.

(21) Appl. No.: 16/835,189

(22) Filed: Mar. 30, 2020

(65) Prior Publication Data
US 2020/0329655 A1 Oct. 22, 2020

Related U.S. Application Data

(60) Provisional application No. 62/834,208, filed on Apr. 15, 2019.

(51) Int. Cl.
| | |
|---|---|
| *A01H 1/00* | (2006.01) |
| *A01H 5/08* | (2018.01) |
| *A01H 1/04* | (2006.01) |
| *A01H 6/82* | (2018.01) |

(52) U.S. Cl.
CPC .............. *A01H 1/04* (2013.01); *A01H 1/00* (2013.01); *A01H 1/1245* (2021.01); *A01H 1/1255* (2021.01); *A01H 5/08* (2013.01); *A01H 6/822* (2018.05)

(58) Field of Classification Search
None
See application file for complete search history.

(56) References Cited

U.S. PATENT DOCUMENTS

| 9,689,045 B2 | 6/2017 | Gabor et al. |
| 2013/0055465 A1 | 2/2013 | Gabor et al. |
| 2014/0272088 A1 | 9/2014 | Eggink et al. |

FOREIGN PATENT DOCUMENTS

| WO | WO2009098685 A2 | 8/2009 |

OTHER PUBLICATIONS

International Search Report and Written Opinion for International App. No. PCT/US20/26916, dated Jul. 23, 2020.
Lefebvre et al., "QTLs for resistance to powdery mildew in pepper under natural and artificial infections," Theor Appl Genet, 2003, 107, 661-666.
Zheng et al., "Loss of Function in Mlo Orthologs Reduces Susceptibility of Pepper and Tomato to Powdery Mildew Disease Caused by Leveillula taurica," Plos One, 2013, 8(7), e70723.
Souza et al., "Resistance to Leveillula taurica in the genus *Capsicum*," Plant Pathology, 2003, 52, 613-619.
Jo et al., "Genetic Mapping of the Powdery Mildew Resistance (PMR1) Gene in Pepper (*Capsicum annuum*)," Capsicum and Eggplant Meeting, Poster Presentation, Keckemet, Hungary, Sep. 12-14, 2016.
Extended European Search Report regarding European App. No. 20791418.5, dated Dec. 21, 2022.
Reddy, et al., Exploitation of AVRDC's Chili Pepper (*Capsicum* spp.) Germplasm in India, J. Taiwan Soc. Hort. Sci. 61(1): 1-10, 2015.

*Primary Examiner* — Phuong T Bui
(74) *Attorney, Agent, or Firm* — Dentons US LLP; Matthew Madsen

(57) ABSTRACT

The present disclosure provides *Capsicum annuum* plants exhibiting increased resistance to *Leveillula taurica*. Such plants comprise novel introgressed genomic regions associated with disease resistance on chromosome 6. In certain aspects, compositions and methods for producing, breeding, identifying, and selecting plants or germplasm with an increased disease resistance phenotype are provided.

14 Claims, 4 Drawing Sheets

Specification includes a Sequence Listing.

POWDERY MILDEW RESISTANT PEPPER PLANTS

CROSS-REFERENCE TO RELATED APPLICATIONS

This application claims the benefit of priority of U.S. Provisional Appl. Ser. No. 62/834,208, filed Apr. 15, 2019, the disclosure of which is hereby incorporated by reference in its entirety.

FIELD OF THE INVENTION

The present invention relates to the field of agriculture and more specifically to methods and compositions for producing pepper plants exhibiting improved resistance to the fungus *Leveillula taurica*, which causes powdery mildew disease.

INCORPORATION OF SEQUENCE LISTING

A sequence listing containing the file named SEMB041WO-revised_ST25.txt, which is 13 kilobytes (measured in MS-Windows®) and created on Jun. 21, 2022, and comprises 33 sequences, is incorporated herein by reference in its entirety.

BACKGROUND OF THE INVENTION

Disease resistance is an important trait in agriculture, particularly for the production of food crops. Although disease resistance alleles have been identified in pepper plants, efforts to introduce these alleles into elite lines are hindered by a lack of specific markers linked to the alleles, linkage drag that leads to unacceptable plant quality and a lack of broad spectrum resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

The present invention provides an agronomically elite *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment. In certain embodiments, said first recombinant chromosomal segment comprises a marker locus selected from the group consisting of marker locus M1 (SEQ ID NO: 5), marker locus M2 (SEQ ID NO: 10), marker locus M3 (SEQ ID NO: 15), marker locus M4 (SEQ ID NO: 20), and marker locus M5 (SEQ ID NO: 25) on chromosome 6. In further embodiments, said *Leveillula taurica* resistance allele is located between 230,204,596 bp and 236,762,169 bp on chromosome 6 of the public pepper CM334 v1.55 map. In yet other embodiments, a recombinant chromosomal segment is provided as described herein, wherein a representative sample of seed comprising said chromosomal segment has been deposited under ATCC Accession No. PTA-125810.

The present invention additionally provides a plant part of an agronomically elite *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment. In certain embodiments, said plant part is a cell, a seed, a root, a stem, a leaf, a fruit, a flower, or pollen. In further embodiments, the invention provides a seed that produces an agronomically elite *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment.

The present invention also provides an agronomically elite *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment, wherein said plant further comprises a second recombinant chromosomal segment on chromosome 4, wherein said second recombinant chromosomal segment comprises an allele conferring improved resistance to *Leveillula taurica* relative to a plant lacking said second recombinant chromosomal segment. In some embodiments, said *Leveillula taurica* resistance allele is in a genomic region flanked by marker locus NE0236790 (SEQ ID NO: 26) and marker locus NE0239147 (SEQ ID NO: 33) on chromosome 4. In other embodiments, said second recombinant chromosomal segment comprises a marker selected from the group consisting of marker locus NE0238899 (SEQ ID NO: 27), marker locus NE0238734 (SEQ ID NO: 28), marker locus NE0240256 (SEQ ID NO: 29), marker locus NE0237985 (SEQ ID NO: 30), marker locus NE0239638 (SEQ ID NO: 31), and marker locus NCANN005704056 (SEQ ID NO: 32) on chromosome 4. The present invention further provides seed that produce the plants described herein.

In addition, the present invention provides a plant part of an agronomically elite *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment, wherein said plant further comprises a second recombinant chromosomal segment on chromosome 4, wherein said second recombinant chromosomal segment comprises an allele conferring improved resistance to *Leveillula taurica* relative to a plant lacking said second recombinant chromosomal segment. In certain embodiments, said plant part is a cell, a seed, a root, a stem, a leaf, a fruit, a flower, or pollen.

The present invention provides a method for producing an agronomically elite *Capsicum annuum* plant with improved resistance to *Leveillula taurica* comprising introgressing into said plant a *Leveillula taurica* resistance allele within a recombinant chromosomal segment flanked in the genome of said plant by marker locus M4 (SEQ ID NO: 20) and marker locus M3 (SEQ ID NO: 15) on chromosome 6, wherein said introgressed *Leveillula taurica* resistance allele confers to said plant resistance to *Leveillula taurica* relative to a plant lacking said allele. In some embodiments, said introgressing comprises crossing a plant comprising said recombinant chromosomal segment with itself or with a second *Capsicum annuum* plant of a different genotype to produce one or more progeny plants and selecting a progeny plant comprising said recombinant chromosomal segment. In other embodiments, selecting a progeny plant comprises detecting nucleic acids comprising marker locus M1 (SEQ ID NO: 5), marker locus M2 (SEQ ID NO: 10), marker locus M3 (SEQ ID NO: 15), marker locus M4 (SEQ ID NO: 20), or marker locus M5 (SEQ ID NO: 25). In further embodiments, the progeny plant is an $F_2$-$F_6$ progeny plant. In some embodiments, said introgressing comprises backcrossing, marker-assisted selection or assaying for said resistance to *Leveillula taurica*. In further embodiments, said backcrossing comprises from 2-7 generations of backcrosses. In other embodiments, said plant further comprises a further introgressed *Leveillula taurica* resistance allele within a recombinant chromosomal segment flanked in the genome of said plant by marker locus NE0236790 (SEQ ID NO: 26) and marker locus NE0239147 (SEQ ID NO: 33) on chromosome 4. The present invention further provides *Capsicum annuum* corn plants obtainable by the methods provided herein.

The present invention also provides a method of selecting a *Capsicum annuum* plant exhibiting resistance to *Leveillula taurica*, comprising crossing the *Capsicum annuum* plant of claim 1 with itself or with a second *Capsicum annuum* plant of a different genotype to produce one or more progeny plants and selecting a progeny plant comprising said *Leveillula taurica* resistance allele. In some embodiments, selecting said progeny plant detecting a marker locus genetically linked to said *Leveillula taurica* resistance allele. In other embodiments, selecting said progeny plant comprises detecting a marker locus within or genetically linked to a chromosomal segment flanked in the genome of said plant by marker locus M4 (SEQ ID NO: 20) and marker locus M3 (SEQ ID NO: 15) on chromosome 6. In further embodiments, said progeny plant is an $F_2$-$F_6$ progeny plant. In yet further embodiments, producing said progeny plant comprises backcrossing.

DETAILED DESCRIPTION

Figure 1:
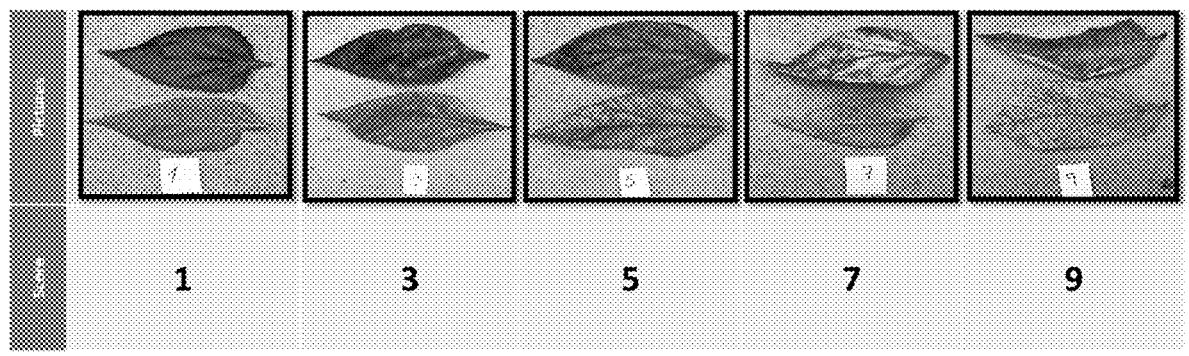
FIG. 1: Shows representative images of pepper plants with varying levels of *Leveillula taurica* infection and their associated disease scores. The disease score is measured on a scale of 1-9, as follows: 1=healthy plants; 3=yellow or necrotic spots on leaves, but no visible sporulation; 5=yellow or necrotic spots on leaves with sporulation inside lesion; 7=sporulation spreading to the downside of the leaf but covering <50% of the leaf; 9=sporulation covering >50% of the leaf surface.

Pepper plants are one of the most popular fruit-bearing plants grown worldwide. Pepper plants are grown in a wide range of climates in open fields as well as in greenhouses. Peppers belong to the genus *Capsicum*, of the nightshade family, Solanaceae (e.g. *Capsicum annuum*). The term "pepper" may refer to the plant as well as its fruit. Peppers are commonly broken down into three groupings: bell peppers, sweet peppers, and hot peppers. Most popular pepper varieties fall into one of these categories, or as a cross between them. However, these groupings are not absolute, as both "hot pepper" and "sweet pepper" encompass members belonging to several different species. Additionally, members of each of the groups may be different cultivars of the same species. For example, the bell pepper, the jalapeno pepper, and the "Thai sweet" all belong to the species *Capsicum annuum*. Hot peppers, including some inedible varieties, are grown for edible as well as ornamental and medicinal uses. While there are pungent (i.e. "hot") varieties of *Capsicum annuum*, many well-known hot peppers are members of different species. For example, both the cayenne pepper and the Tabasco pepper are varieties of *Capsicum frutescens*, while the hottest peppers, including the habanero and naga varieties, are members of *Capsicum chinense*.

Pepper breeding efforts have focused in part on growing pepper plants resistant to diseases such as powdery mildew. Powdery mildew, caused by the fungus *Leveillula taurica*, exhibits a worldwide disease distribution and can affect peppers grown under greenhouse or field conditions.

Symptoms of pepper powdery mildew, caused by the fungus *Leveillula taurica*, during the initial stages of infection may include visible light-green to bright-yellow blotches appearing on upper and lower surfaces of leaves followed by a powdery, white growth caused by the sporulation of the fungus. Under some environmental conditions these areas may later turn necrotic. Infected leaves may also curl upward and exhibit a visible powdery, white growth on the underside of leaves. When lesions are numerous, they often coalesce, resulting in general chlorosis and leaf drop. The disease generally progresses from older to younger leaves. Common commercial fruit production yield losses come from fruits on affected plants being overexposed to sunlight and developing sunscald as well as reduced yield due to leaf loss.

Airborne conidia (asexual fungal spores) from previously infected crops or weeds can be carried long distances by wind and act as initial sources of inoculum. The wide host range of these fungi exacerbate disease spread and reduce the ability of agronomic practice to control disease incidence. Disease control is commonly managed by application of fungicides before infection or immediately after the first symptoms are observed. In addition to the cost of pesticide application, there is increasing social pressure to reduce the pesticide load in the environment.

The invention represents a significant advance in the art by providing plants of the genus *Capsicum* having increased resistance to powdery mildew caused by the fungus *Leveillula taurica*. Such plants can be referred to as plants of powdery mildew resistant pepper varieties. Methods of producing such powdery mildew resistant pepper plants, lines and varieties are further provided. Also disclosed herein are molecular markers that are linked to quantitative trait loci (QTL) contributing to powdery mildew resistance. Through use of such markers, one of skill in the art may increase the degree of powdery mildew resistance in pepper plants and select plants for an increased predisposition for powdery mildew resistance. In particular embodiments, the methods are performed on pepper plants comprising a QTL contributing to powdery mildew resistance found in pepper line PBC167, including, for example, progeny or progenitors of pepper line PBC167.

Previously, *Leveillula taurica* resistance sources have been identified in pepper. A study of the *Leveillula taurica* resistant pepper line H3, for example, uncovered a major resistance QTL on chromosome 6, while additional minor resistance QTLs were found on chromosomes 5, 9, 10, and 12 (Lefebvre et al. 2003). Similarly, a *Leveillula taurica* resistance QTL was identified on LG 1/8 (pepper chromosome 8) in pepper plants derived from *C. fructescens* (U.S. Patent Publication No. 2014/0272088 A1). A major *Leveillula taurica* resistance QTL on chromosome 4 was also identified in the hot pepper variety PBC167 (U.S. Pat. No. 9,689,045), the disclosure of which is incorporated herein by reference in its entirety. However, the resistance QTL on chromosome 4 provides sufficient resistance to *Leveillula taurica* under mild to moderate disease pressure but fails to consistently provide adequate resistance under moderate to high disease pressure.

The present invention represents a significant advance in that it provides, in one embodiment, *Leveillula taurica* resistance in pepper plants conferred by a novel QTL on chromosome 6 as well as novel recombinant chromosomal segments comprising the QTL. The resistance and QTL are distinct from those known in the art, with significantly increased resistance when deployed in combination with the known resistance locus on chromosome 4. This is especially evident in situations where there is moderate to heavy disease pressure. In addition, novel markers for the new locus are provided, allowing the locus to be accurately introgressed and tracked during development of new varieties. As such, the invention permits introgression of the disease resistance locus into potentially any desired pepper genotype.

In certain embodiments, plants are provided herein comprising an introgressed *Leveillula taurica* resistance locus on chromosome 6, wherein the allele confers to the plant increased resistance to *Leveillula taurica* compared to a plant not comprising the locus. In further embodiments, plants are provided comprising combinations of introgressed *Leveillula taurica* resistance loci on chromosomes 6 and 4.

In some embodiments, an introgressed *Leveillula taurica* resistance locus (allele) provided by the invention is defined as located on chromosome 6 within a recombinant chromosomal segment flanked by marker locus M4 (SEQ ID NO: 20) and marker locus M3 (SEQ ID NO: 15). In other embodiments, such a segment can comprise one or more of marker locus M1 (SEQ ID NO: 5), marker locus M2 (SEQ ID NO: 10), and marker locus M3 (SEQ ID NO: 15). Marker locus M4 comprises a SNP change from A to C at 230,204, 596 bp on chromosome 6 of the public pepper CM334 v1.55 map, marker locus M1 comprises a SNP change from T to C at 233,270,768 bp of chromosome 6 of the public pepper CM334 v1.55 map, marker locus M2 comprises a SNP change from T to C at 233,426,022 bp of chromosome 6 of the public pepper CM334 v1.55 map, marker locus M3 comprises an INDEL marker with a 6 bp insertion (AAAGGA) at 236,762,169 bp of chromosome 6 of the public pepper CM334 v1.55 map, marker locus M5 comprises a SNP change from T to C at 235,546,118 bp on chromosome 6 of the public pepper CM334 v1.55 map.

In other embodiments, the invention provides plants comprising the recombinant introgression on chromosome 6 provided herein conferring resistance to *Leveillula taurica* relative to a control plant, such as a plant of the same variety grown under the same conditions but lacking the introgression. Methods of producing the plants described herein are further provided. The invention further provides novel trait-linked markers which can be used to produce plants comprising the recombinant introgression, including the markers shown in Table 1. Other embodiments of the invention provide markers M1 (SEQ ID NO: 5), M2 (SEQ ID NO: 10), M3 (SEQ ID NO: 15), M4 (SEQ ID NO: 20), and M5 (SEQ ID NO: 25), which have been shown to be genetically linked to *Leveillula taurica* resistance in plants.

In other embodiments, the invention provides plants comprising the novel recombinant introgression on chromosome 6 as well as the recombinant introgression on chromosome 4 that is found in line PBC167. Surprisingly, this combination provides robust resistance to *Leveillula taurica* under moderate to heavy disease pressure. Methods of producing such plants comprising the robust resistance are further provided. In certain embodiments the recombinant introgression on chromosome 4 is flanked by marker locus NE0236790 (SEQ ID NO: 26) and marker locus NE0239147 (SEQ ID NO: 33). The invention additionally provides novel trait-linked markers for producing such plants, including the markers shown in Table 2 and markers NE0238899 (SEQ ID NO: 27), NE0238734 (SEQ ID NO: 28), NE0240256 (SEQ ID NO: 29), NE0237985 (SEQ ID NO: 30), NE0239638 (SEQ ID NO: 31), and NCANN005704056 (SEQ ID NO: 32), which are genetically linked to *Leveillula taurica* resistance in plants.

Because genetically diverse plant lines can be difficult to cross and assaying of disease resistance can be particularly challenging, requiring generation of disease-causing conditions that may be difficult to reproduce, the introgression of *Leveillula taurica* resistance alleles into elite lines using conventional breeding methods could require prohibitively large populations and trials for progeny screens with an uncertain outcome. Marker-assisted selection (MAS) is therefore essential for the effective introgression of *Leveillula taurica* resistance alleles into elite cultivars. However, previously known markers for *Leveillula taurica* resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. Genomic Regions, Alleles, and Polymorphisms Associated with Increased Resistance to *Leveillula taurica*

The newly identified QTL on chromosome 6 was found to be flanked by marker M4 (SEQ ID NO: 20), a SNP change from A to G at 230,204,596 bp of the public genome of Pepper CM334v.1.55 genome, which is available from solgenomics.net, and M3 (SEQ ID NO: 15), an INDEL marker with a 6 bp insertion (AAAGGA) at 236,762,169 bp of the public genome of Pepper CM334v.1.55. Interstitial markers M1 (SEQ ID NO: 5), a SNP change from T to C at 233,270,768 bp, M2 (SEQ ID NO: 10), a SNP change from T to C at 233,426,022 bp of the public genome of Pepper CM334v.1.55, and M5 (SEQ ID NO: 25), a SNP change from T to C at 235,546,118 bp of the public genome of Pepper CM334v.1.55 can be used in addition to the flanking markers to select for the resistance QTL on chromosome 6. In one embodiment, the QTL can be found in resistant hot pepper variety. In certain embodiments, a marker is employed that is interstitial between M4 and M3, such as M1, M2, or M5.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from a resistance source, which could be any pepper plant comprising the locus identified herein providing disease resistance. One such example is hot pepper variety PBC167, which is publicly available from the United States Department of Agriculture (USDA) germplasm collection under Accession No. PI640507. The invention further provides markers for identifying and tracking the novel introgression disclosed herein during plant breeding.

In specific embodiments, the markers provided herein within or linked to any of the genomic intervals of the present invention can be used in a variety of breeding efforts that include introgression of genomic regions associated with disease resistance into a desired genetic background. For example, a marker within 30 cM, 25 cM, 20 cM, 16 cM, 15 cM, 10 cM, 5 cM, 2 cM, or 1 cM or less, or within a disease resistance-conferring locus described herein can be used for marker-assisted introgression of genomic regions associated with a disease resistant phenotype.

The present invention provides pepper plants comprising one or more introgressed regions associated with a desired phenotype wherein at least 10%, 25%, 50%, 75%, 90%, or 99% of the remaining genomic sequences carry markers characteristic of the germplasm. Pepper plants comprising an introgressed region comprising regions closely linked to or adjacent to the genomic regions and markers provided herein and associated with resistance to *Leveillula taurica* are also provided.

III. Development of Disease Resistant *Capsicum annuum* Varieties

For most breeding objectives, commercial breeders work within germplasm that is "cultivated type" or "elite." As used herein, "elite" or "cultivated" variety means a variety that has resulted from breeding and selection for superior horticultural performance for use in agriculture. This germplasm is easier to breed because it generally performs well when evaluated for horticultural performance. A number of cultivated pepper types have been developed, which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. For example, non-cultivated pepper lines can provide alleles associated with disease resistance. However, this non-cultivated type may have poor horticultural qualities such as vulnerability to necrosis or low fruit production.

The process of introgressing desirable resistance alleles from non-cultivated lines into elite cultivated lines while avoiding problems with linkage drag or low trait heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked phenotypically or genetically. Thus, Applicants' discovery of accurate markers associated with disease resistance will facilitate the development of pepper plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous for the desired introgression.

Meiotic recombination is essential for plant breeding because it enables the transfer of favorable alleles across genetic backgrounds, the removal of deleterious genomic fragments, and pyramiding traits that are genetically tightly linked. Limited recombination forces breeders to enlarge segregating populations for progeny screens. In the absence of markers, breeders must rely on phenotypic evaluation, which is time-consuming, resource-intensive and not reproducible in every environment, particularly for traits like disease resistance. In contrast markers allow a breeder to select those individuals of interest without having to expose the whole population to phenotypic evaluation. The markers provided by the invention offer an effective alternative and therefore represent a significant advance in the art.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay, making it necessary to work with a combination of marker assays, e.g., haplotype assays. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, single nucleotide polymorphisms (SNPs), insertion/deletion polymorphisms (Indels), restriction fragment length polymorphisms (RFLPs), amplified fragment length polymorphisms (AFLPs), simple sequence repeats (SSRs), simple sequence length polymorphisms (SSLPs), variable number tandem repeats (VNTRs), and random amplified polymorphic DNA (RAPD), isozymes, and other markers known to those skilled in the art. Plant breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita, et al., *Genomics* 8:271-278, 1989), denaturing gradient gel electrophoresis (Myers, EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Capsicum annuum* plant a genotype associated with disease resistance, identify a *Capsicum annuum* plant with a genotype associated with disease resistance, and to select a *Capsicum annuum* plant with a genotype associated with disease resistance. In certain embodiments of methods of the invention, polymorphic nucleic acids can be used to produce a *Capsicum annuum* plant that comprises in its genome an introgressed locus associated with disease resistance. In certain embodiments of the invention, polymorphic nucleic acids can be used to breed progeny *Capsicum annuum* plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in *Capsicum annuum* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz, et al., *Genome Res.* 13:513-523, 2003; Cui, et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Capsicum annuum* plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite line" or "cultivated line" means any line that has resulted from breeding and selection for superior agronomic performance. An "elite plant" refers to a plant belonging to an elite line. Numerous elite lines are available and known to those of skill in the art of *Capsicum annuum* breeding. An "elite population" is an assortment of elite individuals or lines that can be used to represent the state of the art in terms of agronomically superior genotypes of a given crop species, such as a *Capsicum annuum* line. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to Leveillula taurica.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 625 seeds of pepper line SBR-BW19-1046, which comprises the introgression on chromosome 6, as described herein. The deposit was made with the American Type Culture Collection (ATCC), 10801 University Boulevard, Manassas, Va. 20110-2209 USA. The deposit is assigned ATCC Accession No. PTA-125810, and the date of deposit was Mar. 12, 2019. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLE 1

Phenotyping Leveillula taurica Resistance on Chromosome 6

Resistance to Leveillula taurica can be phenotypically determined in seedlings adult plants assay or a seedling assay. Inoculum is prepared by harvesting spores from Leveillula taurica infected leaves of susceptible pepper plants, preferably 4-8 weeks after infection. Conidia were harvested from leaves with abundant white powdery mildew sporulation by washing the symptomatic leaves and collecting the spore suspension, followed by immediate dilution with Tween (1 drop per 100 mL). The conidia suspension was then diluted to $4 \times 10^4$ conidia/mL (4× the normal inoculum concentration), a concentration which mimics high disease pressure.

For the adult plant assay, seedlings with 4-5 leaves of similar size were selected and transplanted to the greenhouse. Experimental and control plants were inoculated with conidia suspension when the first fruit started to set, followed by a second inoculation two weeks later. The experimental plants were surrounded by a border of susceptible plants to further spread disease. Plants were allowed to develop symptoms in a temperature and humidity-controlled greenhouse. Sporulation density and the number of spots per leaf were evaluated 8 weeks post inoculation according to a scale from 1 to 9 as follows: 1=healthy plants; 3=yellow or necrotic spots on leaves, but no visible sporulation; 5=yellow or necrotic spots on leaves with sporulation inside lesion; 7=sporulation spreading to the downside of the leaf but covering <50% of the leaf; 9=sporulation covering >50% of the leaf surface (FIG. 1).

For the seedling assay, seeds were germinated in peat with vermiculite in trays with 40 alveoli. When seedlings reached the $3^{rd}$ leaf stage, they were moved from the nursery to the greenhouse. Only seedlings with fully expanded $3^{rd}$ leaves were sprayed with inoculum. In addition, seedlings having more than three leaves were trimmed of the excess leaves prior to inoculation. Inoculated seedlings were maintained for 48 hours in the greenhouse with high humidity at 28° C. (day) and 16° C. (night). The humidity level was subsequently adjusted to be high at night only. Throughout the course of the experiment, the seedlings were maintained out of direct sunlight with daily watering to keep humidity in the soil. The seedlings were fertilized weekly, beginning about 14-21 days after sowing, and any new growth beyond the original three inoculated leaves was removed. Sporulation density and the number of spots per leaf were evaluated when susceptible controls were fully infected (4-5 weeks post inoculation), according to a scale from 1 to 9 as follows: 1=healthy plants; 3=yellow or necrotic spots on leaves, but no visible sporulation; 5=yellow or necrotic spots on leaves with sporulation inside lesion; 7=sporulation spreading to the downside of the leaf but covering <50% of the leaf; 9=sporulation covering >50% of the leaf surface (FIG. 1).

EXAMPLE 2

QTL Mapping of the *Leveillula taurica* Resistance Locus on Chromosome 6

The *Leveillula taurica* resistance conferred by the QTL on chromosome 4 from PBC167 is not adequate under heavy *Leveillula taurica* disease pressure in elite lines (FIG. 2). To determine whether additional loci from PBC167 contribute to *Leveillula taurica* resistance, a BC1F2:F3 mapping population was developed from an initial cross between the PBC167 resistance donor and an elite susceptible parent. The 265 families that comprised this mapping population were tested for *Leveillula taurica* resistance in a random complete block design trial with three replications and five plants per plot. These families were also genotyped using 143 markers located across the genome. The subsequent QTL analysis confirmed the known major resistance locus on chromosome 4, but also identified a minor resistance QTL that mapped to a 8.2cM region located between markers M4 and M5 on chromosome 6. M4 is a SNP marker with a [A/C] change at 230,204,596 bp on chromosome 6 of the public pepper CM334 v1.55 map. M5 is a SNP marker with a [TIC] change at 235,546,118 bp on chromosome 6 of the public pepper CM334 v1.55 map (Table 1).

To further map the newly identified region on chromosome 6, a subset containing 20 families that were homozygous for the resistance QTL on chromosome 4 and had a recombination event between markers M4 and M5 on chromosome 6 were selected from the BC1F2:F3 population. From each family, plants that were homozygous for the recurrent parent and donor parent alleles on either side of the recombination event were selected. Phenotypic trials were performed in the greenhouse using an adult plant assay and a random 4-replication complete block design. The susceptible elite parent, resistance donor PBC167, susceptible line Yolo Wonder B, and a line derived from H3 (resistant) were used as controls. To ensure that all plants were exposed equally to *Leveillula taurica* spores, 350 susceptible plants were placed in rows throughout the trial. The plants were evaluated for their resistance to *Leveillula taurica* and genotyped for markers located within the rough mapped QTL region on chromosome 6. Subsequent QTL analysis further defined the resistance QTL to a 6.5cM region on chromosome 6. Additional markers, including M1 and M3, were developed to increase the resolution in this region. M1 is a SNP marker with a [TIC] change at 233,270,768 bp of chromosome 6 on the public pepper CM334 v1.55 map. M3 is an INDEL marker with a 6 bp insertion (AAAGGA) at 236,762,169 bp of chromosome 6 of the public pepper CM334 v1.55 map. Marker M2 can also be used to select for the *Leveillula taurica* resistance introgression on chromosome 6. M2 is a SNP marker with a [T/C] change at 233,426,022 bp of chromosome 6 on the public pepper CM334 v1.55 map (Table 1).

The newly-identified QTL on chromosome 6 was observed to have a low effect on resistance, as it was not always detectable under normal testing conditions. Furthermore, the effect of QTL on chromosome 6 is potentially masked by the effect of the known QTL on chromosome 4 when both loci are present in sub-optimal disease pressure. A second round of fine mapping of the QTL on chromosome 6 was performed in the absence of the QTL on chromosome 4. 20 BC3F2 recombinant lines derived from the same cross that produced the earlier mapping population were selected. Each of the BC3F2 recombinant lines that were selected lacked the resistance QTL on chromosome 4 and had a different recombination breakpoint between markers M4 and M5 on chromosome 6. The phenotypic trials were performed in the greenhouse using a seedling assay and a random 4-replication complete block design. Tissue samples for genotypic analysis were taken 19 days after sowing. About 25 days after sowing, seedlings were inoculated with a 10,000 spores/mL suspension of *Leveillula taurica*. Sporulation density and the number of spots per leaf were evaluated 22 days post inoculation, according to a scale from 1 to 9 as follows: 1=healthy plants; 3=yellow or necrotic spots on leaves, but no visible sporulation; 5=yellow or necrotic spots on leaves with sporulation inside lesion; 7=sporulation spreading to the downside of the leaf but covering <50% of the leaf; 9=sporulation covering >50% of the leaf surface. Subsequent QTL analysis placed the resistance QTL between markers M1 and M3 on chromosome 6.

TABLE 1

Markers to track PBC167-derived *Leveillula taurica* resistance on chromosome 6.

| Marker | Chr | Favorable Allele | SNP Change | SNP Position in Marker (bp) | SNP Position in Public Genome (bp) | Fwd Primer (SEQ ID NO) | Rev Primer (SEQ ID NO) | Probe 1 (SEQ ID NO) | Probe 2 (SEQ ID NO) | Marker Sequence (SEQ ID NO) |
|---|---|---|---|---|---|---|---|---|---|---|
| M1 | 6 | C | [T/C] | 301 | 233,270,768 | 1 | 2 | 3 | 4 | 5 |
| M2 | 6 | T | [T/C] | 301 | 233,426,022 | 6 | 7 | 8 | 9 | 10 |
| M3 | 6 | AAAGGA | [AAAGGA/******] | 152 | 236,762,169 | 11 | 12 | 13 | 14 | 15 |
| M4 | 6 | A | [A/C] | 175 | 230,204,596 | 16 | 17 | 18 | 19 | 20 |
| M5 | 6 | C | [T/C] | 152 | 235,546,118 | 21 | 22 | 23 | 24 | 25 |

Forward primer TGACCCATCGCAAGCCATTT (SEQ ID NO: 1), reverse primer TGACCCATCGCAAGCCATTT (SEQ ID NO: 2), probe 1 CCTGCACAATTTTA (SEQ ID NO: 3), and probe 2 CCTGCACGATTTTA (SEQ ID NO: 4) are used with M1. For M1, the marker sequence is shown in SEQ ID NO: 5. Forward primer CCACACATTGGAGGAGCTAGAATTT (SEQ ID NO: 6), reverse primer TCCGCCGAGGTTAAAATTACTTCTT (SEQ ID NO: 7), probe 1 AGGTTGAACATTTAGTATATATACG (SEQ ID NO: 8), and probe 2 TTGAACATTTAGTACATATACG (SEQ ID NO: 9) are used with M2. For M2, the marker sequence is shown in SEQ ID NO: 10. Forward primer GCAAGTTGAGCGTACTGATTACTGA (SEQ ID NO: 11), reverse primer CCGACAACAGTCGCAGAAGTTATT (SEQ ID NO: 12), probe 1 ACGCTTCCTTTTCCTTTG (SEQ ID NO: 13), and probe 2 ACGCTTCCTTTGCTACTA (SEQ ID NO: 14) are used with M3. For M3, the marker sequence is shown in SEQ ID NO: 15. Forward primer GTTATCTTTTATGCGACTTGTGATACTGTAGA (SEQ ID NO: 16), reverse primer TGTTGCTGTTTAAAGTCTAGGAGCTT (SEQ ID NO: 17), probe 1

AGAACTTTAGATTAAAAGTCG (SEQ ID NO: 18), and probe 2 ACTTTAGATTCAAAGTCG (SEQ ID NO:19) are used with M4. For M4, the marker sequence is shown in SEQ ID NO: 20. Forward primer TGCAGAGTCCT-TAAACAAAAAGTAACCT (SEQ ID NO: 21), reverse primer AGGCCTCCTGAAACAACAGAAAA (SEQ ID NO: 22), probe 1 AAAATGCAGACATTCTGAAC (SEQ ID NO: 23), and probe 2 ATGCAGACACTCTGAAC (SEQ ID NO: 24) are used with M5. For M5, the marker sequence is shown in SEQ ID NO: 25.

EXAMPLE 3

Figure 2:
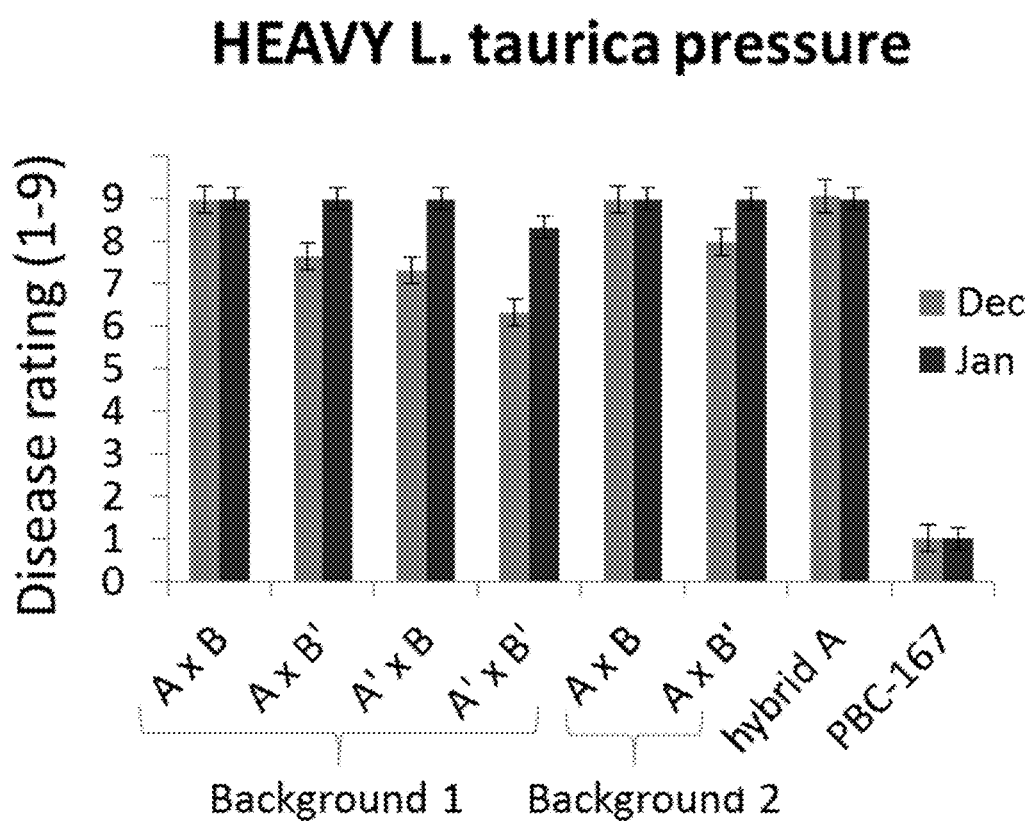
FIG. 2: Shows disease scores of pepper plants comprising 0, 1 (heterozygous), or 2 (homozygous) copies of the *Leveillula taurica* resistance allele on chromosome 4 under high disease pressure. The "" symbol next to the "A" and "B" designations indicates that the resistance allele is present in the parent plant of the hybrid cross. Hybrid A is a publicly available commercial sweet pepper variety that is annotated as having intermediate *L. taurica* resistance, but was used as the susceptible control in these experiments. The donor line PBC167 was used as the resistant control. The disease score was measured on a scale of 1-9, where 1 is fully resistant and 9 is fully susceptible.
Figure 3:
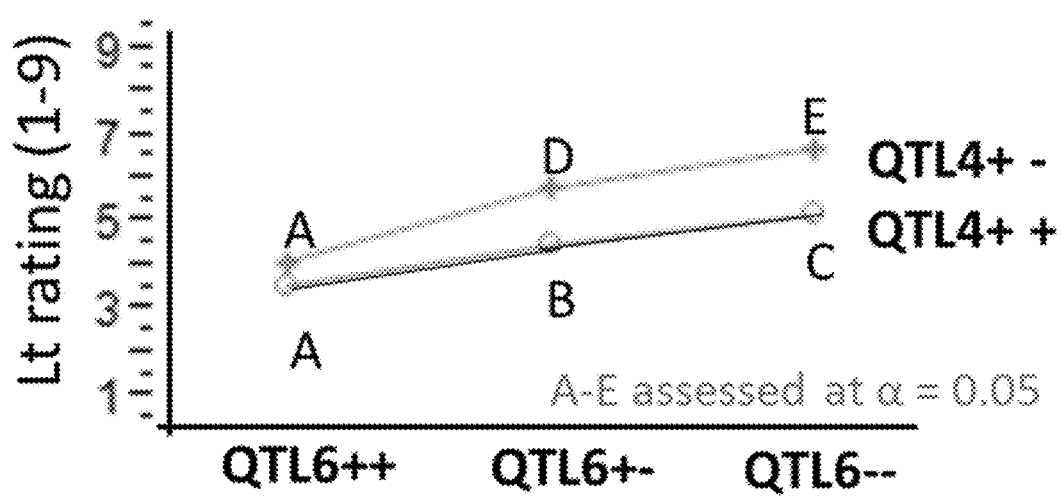
FIG. 3: Shows disease scores of pepper plants with varying genetic backgrounds under high *Leveillula taurica* disease pressure. The pepper population used in this experiment comprise varying combinations of the *Leveillula taurica* resistance QTLs on chromosomes 4 and 6. The letters in the figure indicate significant differences between groups. "+" indicates the presence of the resistance allele; "−" indicates the presence of the susceptible allele.

Deployment of the Chromosome 6 Locus in Combination with the Chromosome 4 Locus The resistance conferred by the QTL on chromosome 4 is not always adequate under heavy *Leveillula taurica* disease pressure in elite lines (FIG. 2). The addition of the resistance QTL on chromosome 6 does not confer an added benefit under intermediate disease pressure, but surprisingly conferred an additional level of resistance under heavy disease pressure (FIG. 3). Phenotypic trials were performed in the greenhouse as described in Example 1, utilizing the susceptible recurrent parent and resistance donor PBC167 as controls. In this study, the recurrent parent scored a disease rating of 9 and the resistance donor PBC167 scored a disease rating of 1.

Figure 4:
FIG. 4: Shows representative images of pepper plants with varying genetic backgrounds exposed to high *Leveillula taurica* disease pressure. The image on the left shows plants that are heterozygous for the resistance QTLs on chromosomes 4 and 6. These plants were resistant to infection and were therefore given a disease rating of 1-2. The center image shows plants that are heterozygous for the resistance QTL on chromosome 4 and lacking the resistance QTL on chromosome 6. These plants have yellow or necrotic spots on leaves with sporulation inside lesions and were given a disease rating of 5. The image on the right shows plants of Hybrid A, a publicly available sweet pepper variety annotated as having intermediate *L. taurica* resistance. These plants show severe disease symptoms under heavy disease pressure and were given a disease rating of 9.

The locus on chromosome 6 was introgressed into various elite lines to evaluate novel hybrid combinations in a range of genetic backgrounds. Phenotypic trials were performed in the greenhouse as described in Example 1, utilizing the susceptible recurrent parent and resistance donor PBC167 as controls. These studies confirm that the addition of the resistance QTL on chromosome 6 to the resistance QTL on chromosome 4 consistently conferred an additional level of resistance under heavy *Leveillula taurica* disease pressure in a range of genetic backgrounds (FIG. 4).

The *Leveillula taurica* resistance conferred by the novel locus identified on chromosome 6 may therefore be stacked with the resistance locus on chromosome 4 to produce elite lines having increased resistance to *Leveillula taurica* that is consistent under all disease pressures. Table 2 shows markers associated with the PBC167-derived *Leveillula taurica* resistance QTL on chromosome 4 and can be used for selection of the locus. The identification of the *Leveillula taurica* resistance QTL on chromosome 4 and markers associated with the locus is described in U.S. Pat. No. 9,689,045, the disclosure of which is incorporated herein by reference in its entirety.

TABLE 2

Markers to track PBC167-derived *Leveillula taurica* resistance on chromosome 4.

| Marker | Chromosome | Genetic Position (cM) | Favorable Allele | Marker Sequence (SEQ ID NO) |
|---|---|---|---|---|
| NE0236790 | 4 | 21.56183958 | TT (recurrent parent) | 26 |
| NE0238899 | 4 | 24.87135151 | GG | 27 |
| NE0238734 | 4 | 24.87248992 | GG | 28 |
| NE0240256 | 4 | 25.1081287 | CC | 29 |
| NE0237985 | 4 | 25.17303092 | CC | 30 |
| NE0239638 | 4 | 25.88460917 | GG | 31 |

TABLE 2-continued

Markers to track PBC167-derived *Leveillula taurica* resistance on chromosome 4.

| Marker | Chromosome | Genetic Position (cM) | Favorable Allele | Marker Sequence (SEQ ID NO) |
|---|---|---|---|---|
| NCANN005704056 | 4 | 25.88461 | CC | 32 |
| NE0239147 | 4 | 26.81001479 | TT (recurrent parent) | 33 |

EXAMPLE 4

Comparison of *Leveillula taurica* Resistance Loci from H3 and PBC167

*Leveillula taurica* resistance sources have previously been identified in pepper. A major *Leveillula taurica* resistance QTL was identified on chromosome 6 in line H3 (Lefebvre et al. 2003). To determine whether the QTL on chromosome 6 from line PBC167 is the same as the QTL from line H3, a mapping population was developed as described in Lefebvre using *Leveillula taurica* susceptible line HV-12, which is a double haploid line derived from the $F_1$ generation of a cross between H3 and "Vania Vania". Subsequent QTL analysis identified three resistance QTLs, including the QTL on chromosome 6 described in Lefebvre. Subsequent studies confirmed that the resistance QTL on chromosome 6 from H3 on is a major resistance QTL and can explain up 26% of the phenotypic variation. In contrast, the major *Leveillula taurica* resistance QTL from PBC167 is located on chromosome 4. The minor QTL on chromosome 6 from PBC167 only visibly influences *Leveillula taurica* resistance under heavy disease pressure.

Since the loci on chromosome 6 from H3 and PBC167 are located in a similar chromosomal region, fingerprinting analysis of this region was performed. The subsequent comparative analysis based on 46 markers showed that H3 and PBC167 only showed 65.7% similarity in this region, leading to the conclusion that the resistance loci on chromosome 6 derived from lines H3 and PBC167 are distinct.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cultivated *Capsicum annuum* plant comprising at least a first recombinant chromosomal segment on chromosome 6, wherein said first recombinant chromosomal segment comprises an allele conferring resistance to *Leveillula taurica* relative to a plant lacking said recombinant chromosomal segment, wherein the allele is flanked in said segment by marker locus M4 having SEQ ID NO:20 and marker locus M3 having SEQ ID NO:15, and wherein a representative sample of seed comprising said chromosomal segment has been deposited under ATCC Accession No. PTA-125810.

2. The plant of claim 1, wherein said first recombinant chromosomal segment further comprises a marker locus selected from the group consisting of marker locus M1 having SEQ ID NO: 5, marker locus M2 having SEQ ID NO: 10 and marker locus M5 having SEQ ID NO: 25 on chromosome 6.

3. The plant of claim 1, wherein said *Leveillula taurica* resistance allele is located between 230,204,596 bp and 236,762,169 bp on chromosome 6 of the public pepper CM334 v1.55 map.

4. A plant part of the plant of claim 1, wherein said plant part comprises said first recombinant chromosomal segment.

5. The plant part of claim 4, wherein said plant part is a cell, a seed, a root, a stem, a leaf, a fruit, a flower, or pollen.

6. A seed that produces the plant of claim 1.

7. A method for producing a cultivated *Capsicum annuum* plant comprising introgressing into said plant an allele conferring resistance to *Leveillula taurica* within a recombinant chromosomal segment flanked in the genome of said plant by marker locus M4 having SEQ ID NO: 20 and marker locus M3 having SEQ ID NO: 15 on chromosome 6, wherein said introgressed *Leveillula taurica* resistance allele confers to said plant resistance to *Leveillula taurica* relative to a plant lacking said recombinant chromosomal segment, and wherein a representative sample of seed comprising said chromosomal segment has been deposited under ATCC Accession No. PTA-125810.

8. The method of claim 7, wherein said introgressing comprises:
   a) crossing the plant comprising said recombinant chromosomal segment with itself or with a second *Capsicum annuum* plant of a different genotype to produce one or more progeny plants; and b) selecting a progeny plant comprising said recombinant chromosomal segment.

9. The method of claim 8, wherein selecting the progeny plant comprises detecting marker locus M1 having SEQ ID NO: 5, marker locus M2 having SEQ ID NO: 10, marker locus M3 having SEQ ID NO: 15, marker locus M4 having SEQ ID NO: 20, or marker locus M5 having SEQ ID NO: 25.

10. The method of claim 8, wherein said introgressing comprises backcrossing or marker-assisted selection.

11. The method of claim 10, wherein the progeny plant is an $F_2$-$F_6$ progeny plant or wherein said backcrossing comprises 2-7 generations of backcrosses.

12. A method of selecting a *Capsicum annuum* plant exhibiting resistance to *Leveillula taurica*, comprising:
   a) crossing the *Capsicum annuum* plant of claim 1 with itself or with a second *Capsicum annuum* plant of a different genotype to produce one or more progeny plants; and
   b) selecting a progeny plant comprising said recombinant chromosomal segment.

13. The method of claim 12, wherein selecting said progeny plant comprises:
   detecting marker locus M1 having, SEQ ID NO: 5, marker locus M2 having SEQ ID NO: 10, marker locus M3 having SEQ ID NO: 15, marker locus M4 having SEQ ID NO: 20, or marker locus M5 having SEQ ID NO: 25.

14. The method of claim 12, wherein said progeny plant is an F2-P6 progeny plant.

* * * * *

UNITED STATES PATENT AND TRADEMARK OFFICE
CERTIFICATE OF CORRECTION

| | | |
|---|---|---|
| PATENT NO. | : 11,612,120 B2 | Page 1 of 1 |
| APPLICATION NO. | : 16/835189 | |
| DATED | : March 28, 2023 | |
| INVENTOR(S) | : Just et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 199 days.

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tgacccatcg caagccattt                                                   20

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
cgacaatgct ttccttttca tcact                                             25

<210> SEQ ID NO 3
<211> LENGTH: 14
<212> TYPE: DNA
<213> ORGANISM: Artificial Sequence
<220> FEATURE:
<223> OTHER INFORMATION: Probe

<400> SEQUENCE: 3
cctgcacaat ttta                                                         14

<210> SEQ ID NO 4
<211> LENGTH: 14
<212> TYPE: DNA
<213> ORGANISM: Artificial Sequence
<220> FEATURE:
<223> OTHER INFORMATION: Probe

<400> SEQUENCE: 4
cctgcacgat ttta                                                         14

<210> SEQ ID NO 5
<211> LENGTH: 602
<212> TYPE: DNA
<213> ORGANISM: Capsicum annuum
<220> FEATURE:
<221> NAME/KEY: misc_feature
<222> LOCATION: (88)..(89)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
```

```
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (574)..(576)
<223> OTHER INFORMATION: n is a, c, g, or t

<400> SEQUENCE: 5
aaaaaaaggg tgggagtgga gagatgacta agggaagttt gaggaggtag ggaaaagaaa      60
gacaattgtt ttatttcttt cttctgtnnc ccaagaaacc cattttcgt anccccccc      120 cnccggaccn aaacatggac agttttatta ttggatttca tgaggattaa agtgccacag     180
aaatagtcaa aggcttattc ntagnacctc aaaatgtttc aatgagattc aattgatata     240
gggtattagg agtattttct tgagatccac gtcatgaccc atcgcaagcc atttttaaaat    300 ctgtgcaggc acacactgat ctcctgagtg atgaaaagga aagcattgtc gaggatgcgg    360
atggtgagat gttcgatttt cagctttgtt gantttaatt gtggttatac ttgagataat    420
aacctgctct gttcttatag atcaccctga agaagatgaa gaagctggag aaattgtcct    480
gcagcagtta ccttgggagg gaactgatcg agattatgaa tatgaggagg tactttctta    540
attgttcgta ttttctgcat atacctgcna agannnactt ttagaatgca ctagattgtc    600
ca                                                                   602

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ccacacattg gaggagctag aattt                                           25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
tccgccgagg ttaaaattac ttctt                                           25

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
aggttgaaca tttagtatat atacg                                           25

<210> SEQ ID NO 9
<211> LENGTH: 22
<212> TYPE: DNA
<213> ORGANISM: Artificial Sequence
<220> FEATURE:
```

<223> OTHER INFORMATION: Probe

<400> SEQUENCE: 9
ttgaacattt agtacatata cg          22

<210> SEQ ID NO 10
<211> LENGTH: 601
<212> TYPE: DNA
<213> ORGANISM: Capsicum annuum
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t

<400> SEQUENCE: 10
gcaactgcag attctccggc aggttcaaag ccgacggtaa tcgaaccgga gaaagtcgat     60
tacttcaact tgccttgtcc tgttccttan gaagaaatta atcgtgaagt tataagttag    120
tattttactt catctctcta tttcattgcc tgttttata attttnataa ccatgttgtc    180
agggtcagct tgcatgcatt ctcccacaca ttggaggagc tagaattttc attcattaaa    240
ggggtttgaa aaataaaaaa cnaaacacac gaagcatcga gggaggttga acatttagta    300
tatatacgtt aaataaagaa gaagtaattt taacctcggc ggagctagaa ttttcacttg    360
ttaaggggt tcaaaaaata ggctcattgt tatgaatcaa ttgattatta gcctgtttgg    420
acaaataatt tgttaatcca atcgattatt gacctgtttg gccaagcttt tgggaggtga    480
aaagtgttta ttttaaaaaa gttattatgt taagaacttt ggctaagctt ttgaagaaaa    540
ntaagtncttt atgagggtag tataagttgt ttttcaatag ccaaaaagt ggaaaagcta    600
c                                                                   601

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gcaagttgag cgtactgatt actga          25

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ccgacaacag tcgcagaagt tatt          24

```
<210> SEQ ID NO 13
<211> LENGTH: 18
<212> TYPE: DNA
<213> ORGANISM: Artificial Sequence
<220> FEATURE:
<223> OTHER INFORMATION: Probe

<400> SEQUENCE: 13
acgcttcctt ttcctttg                                                  18

<210> SEQ ID NO 14
<211> LENGTH: 18
<212> TYPE: DNA
<213> ORGANISM: Artificial Sequence
<220> FEATURE:
<223> OTHER INFORMATION: Probe

<400> SEQUENCE: 14
acgcttcctt tgctacta                                                  18

<210> SEQ ID NO 15
<211> LENGTH: 307
<212> TYPE: DNA
<213> ORGANISM: Capsicum annuum
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t

<400> SEQUENCE: 15
cggagnaagt agggtaaaga gtntcgcgtc tcatgttgta gtgtattgtc atcataaatt     60 tcgattttc tgcttcttag tcacattaga gtttggtttg cttaaagcaa gttgagcgta    120
ctgattactg agnnaatggt tcgatagtag caaaggaaaa ggaagcgtaa taacttctgc    180
gactgttgtc ggtgattaat aacataataa tgacaggata gaaggtttca ncttatttca    240
gccatacggc aatccattgc cttttaagac tatcctaagg agaccgattt cgagctctac    300 gtantca                                                             307

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
gttatctttt atgcgacttg tgatactgta ga                                  32

<210> SEQ ID NO 17
```

```
<211> LENGTH: 26
<212> TYPE: DNA
<213> ORGANISM: Artificial Sequence
<220> FEATURE:
<223> OTHER INFORMATION: Primer

<400> SEQUENCE: 17
tgttgctgtt taaagtctag gagctt                                            26

<210> SEQ ID NO 18
<211> LENGTH: 21
<212> TYPE: DNA
<213> ORGANISM: Artificial Sequence
<220> FEATURE:
<223> OTHER INFORMATION: Probe

<400> SEQUENCE: 18
agaactttag attaaaagtc g                                                 21

<210> SEQ ID NO 19
<211> LENGTH: 18
<212> TYPE: DNA
<213> ORGANISM: Artificial Sequence
<220> FEATURE:
<223> OTHER INFORMATION: Probe

<400> SEQUENCE: 19
actttagatt caaagtcg                                                     18

<210> SEQ ID NO 20
<211> LENGTH: 433
<212> TYPE: DNA
<213> ORGANISM: Capsicum annuum

<400> SEQUENCE: 20
tgtctgtctc attctgccca agcagaaact taacaatctg catatgtcaa aggaaacagt       60
taatgacagg taaccagctg ccttattttt cggcttacta gtctcacttt ttgggaacta      120
ttatcagtag ttatctttta tgcgacttgt gatactgtag aagaactttta gattaaaagt     180 cgatgaaaaa gctcctagac tttaaacagc aacaaaacct acatatatgc cagaaaacag      240
catacctgag ctcttccttt ccgagctgca atgtgcaatg ctgtattgcc ctttgtgtca      300 acgctatttta tcaacttagc gtctgctcta gtcagtcct ccacaacctc aaggttttgt     360
cccttgacag ccatgtgaag tgcagtctgc ccctttttat ccatccggct cgctatcact     420
gcctccttta ttc                                                         433

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
tgcagagtcc ttaaacaaaa agtaacct                                          28

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
```

```
aggcctcctg aaacaacaga aaa                                            23
```

<210> SEQ ID NO 23
<211> LENGTH: 20
<212> TYPE: DNA
<213> ORGANISM: Artificial Sequence
<220> FEATURE:
<223> OTHER INFORMATION: Probe

<400> SEQUENCE: 23

```
aaaatgcaga cattctgaac                                                20
```

<210> SEQ ID NO 24
<211> LENGTH: 17
<212> TYPE: DNA
<213> ORGANISM: Artificial Sequence
<220> FEATURE:
<223> OTHER INFORMATION: Probe

<400> SEQUENCE: 24

```
atgcagacac tctgaac                                                   17
```

<210> SEQ ID NO 25
<211> LENGTH: 541
<212> TYPE: DNA
<213> ORGANISM: Capsicum annuum
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 25

```
tctgccccga gatgggaatg attcttgcaa atgcttctgc tgtgggcatg cagccaaagt     60
ctgatcaaac tcctgtctcc aaggtgtctt ttttgcagag tccttnaaca aaaagtaacc    120
tgttatcctt ttgcatgaga aaatgcagac actctgaact tttctgcaat ttttctgttg    180
tttcaggagg ccttnagatc atacgaacta gtatttgatg cagtttacac ccctagaaac    240
acacggttat tgcaggaggc tgcagaggtt ggagctacag ttgtgagtgg ggttgagatg    300
ttcgtcaggc aagcactcgg tcagtttaaa ttgttcaccg acggattagg tagctattct    360
ctcctctcta taatttattt acaagaaatt caaagaacct tctgtcccct agccccatat    420
attttgggtt gggggcaata tatttaagca gtgaacataa ctgaagctct attatggaag    480
taaatagtga agcttatacg caaaacttag ctgaacttga cttggttgat tcttaatctc    540
t                                                                   541
```

<210> SEQ ID NO 26
<211> LENGTH: 121
<212> TYPE: DNA
<213> ORGANISM: Capsicum annuum
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 26

```
cgatacatgc gcaccactcg acatcttttg tggttctcaa gataacaatc gcaggtaaca        60
kcatctgtaa atccaataga acaacttggn ggtaataata ttccctnaga acacccaagc       120
a                                                                      121
```

<210> SEQ ID NO 27
<211> LENGTH: 121
<212> TYPE: DNA
<213> ORGANISM: Capsicum annuum

<400> SEQUENCE: 27

```
aaaattgcct tagtacgaat taatactctt atatattctc aaaagacata tacccagacc        60
rtacttgtgg gattacaccg gctatgttgt ggttgttttg tgaagacata tttaagtact       120
c                                                                      121
```

<210> SEQ ID NO 28
<211> LENGTH: 121
<212> TYPE: DNA
<213> ORGANISM: Capsicum annuum
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 28

```
gttaagcttc tgtgaagcca aaagtnttt tttnncgaag tgtttagtta aaaaagttgc         60
rttgtttggc caagctttta ggaaaaagat aagtatttcg agtcgttgta gaaactgcac       120
t                                                                      121
```

<210> SEQ ID NO 29
<211> LENGTH: 121
<212> TYPE: DNA
<213> ORGANISM: Capsicum annuum

<400> SEQUENCE: 29

```
ctgttcaaga gcaattcagt catttgttct tcaggtaatc ttgtttattc ccaaattgtg        60
scaatcaatt tggttctcat cattggtatc agagacctaa tcatctgacc tgtgcgatgg       120
g                                                                      121
```

<210> SEQ ID NO 30
<211> LENGTH: 121
<212> TYPE: DNA
<213> ORGANISM: Capsicum annuum
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 30

```
tacacnggta aaactgacaa ggcatcagcg ttagccaata atgaactttt agcgcggaac        60
ytcaagtgac caagtgcatg aaaccaaatc aagaaggtaa agatatgntg atcacctgaa       120
t                                                                      121
```

```
<210> SEQ ID NO 31
<211> LENGTH: 121
<212> TYPE: DNA
<213> ORGANISM: Capsicum annuum

<400> SEQUENCE: 31
tggatatagg aaagatcact tagaaattca acaatctttt tcgtctttaa gagcctgtag        60
rcttctttag catctacaca tcaaaattct ccagacattt caaattatat acagtccacg       120
a                                                                      121

<210> SEQ ID NO 32
<211> LENGTH: 218
<212> TYPE: DNA
<213> ORGANISM: Capsicum annuum
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 32
atgcatgagg gcaatacaag cnttgaatcg aaatgactgt ttaatctcgt ggactgtata        60
taatttgaaa tgtctggaga attttgatgt gtagatgcta aagaagncta caggctcyta       120
aagacgaaaa agattgttga atttctaagt gatctttcct atatccaccc ctaagctgcc       180
agcgctgggg gttcctttct cttggttggc cttcctag                              218

<210> SEQ ID NO 33
<211> LENGTH: 121
<212> TYPE: DNA
<213> ORGANISM: Capsicum annuum

<400> SEQUENCE: 33
actcttttat tcgtaatgtt catagacgaa agagacgatc cttcgctcct gtgagcagga        60
yggtgttcca atgtgcaagg ccctttcctg aagaggtcga aaattcacga cccattcata       120
g                                                                      121
```